(12) United States Patent
Jenkner

(10) Patent No.: US 11,517,490 B2
(45) Date of Patent: Dec. 6, 2022

(54) MARINE RESCUE PATIENT ISOLATION APPARATUS

(71) Applicant: ISOVAC PRODUCTS LLC, Romeoville, IL (US)

(72) Inventor: Peter Jenkner, Downers Grove, IL (US)

(73) Assignee: ISOVAC PRODUCTS LLC, Romeoville, IL (US)

(*) Notice: Subject to any disclaimer, the term of this patent is extended or adjusted under 35 U.S.C. 154(b) by 714 days.

(21) Appl. No.: 16/494,028

(22) PCT Filed: Mar. 15, 2018

(86) PCT No.: PCT/US2018/022674
§ 371 (c)(1),
(2) Date: Sep. 13, 2019

(87) PCT Pub. No.: WO2018/170287
PCT Pub. Date: Sep. 20, 2018

(65) Prior Publication Data
US 2020/0085660 A1  Mar. 19, 2020

Related U.S. Application Data

(60) Provisional application No. 62/471,421, filed on Mar. 15, 2017.

(51) Int. Cl.
*A61G 10/00* (2006.01)
*A61G 10/02* (2006.01)
(Continued)

(52) U.S. Cl.
CPC ............ *A61G 10/005* (2013.01); *A61G 1/04* (2013.01); *A61G 3/008* (2013.01); *A61G 10/02* (2013.01);
(Continued)

(58) Field of Classification Search
CPC ...... A61G 10/00–04; A61G 11/00–009; B64D 25/00–20; B64D 7/00–08
See application file for complete search history.

(56) References Cited

U.S. PATENT DOCUMENTS 4,895,171 A * 1/1990 Onik ................. A61F 17/00
5/413 R
5,948,707 A 9/1999 Crawley et al.
(Continued)

FOREIGN PATENT DOCUMENTS

TW          514522 B      12/2002

OTHER PUBLICATIONS

McDevitt, "Extreme Design—The Ebola Bag" (https://www.outinunder.com/content/extreme-design-ebola-bag). (Year: 2016).*
(Continued)

*Primary Examiner* — Thaddeus B Cox
(74) *Attorney, Agent, or Firm* — Pauley Erickson & Swanson

(57) ABSTRACT

A patient isolation unit (PIU) for use in marine rescues. The PIU of this invention is useful to safely transport personnel exposed to, or potentially exposed to, an identified and/or known infectious agent or chemical warfare agent (CWA) on marine vessels and/or aircraft such as Coast Guard boasts, cutters and aircraft. The PIU has a generally tapered tubular shape compatible with wire rescue baskets conforming in shape to the human body and into which an injured, sick, or disabled person can be safely strapped, such as the Stokes litter rescue basket for hoisting and fit in rotary wing aircraft.

20 Claims, 5 Drawing Sheets

(51) Int. Cl.
  *B64D 7/00*    (2006.01)
  *B64D 25/02*   (2006.01)
  *A61G 1/04*    (2006.01)
  *A61G 3/00*    (2006.01)
  *A61M 16/10*   (2006.01)

(52) U.S. Cl.
  CPC ............ *A61M 16/105* (2013.01); *B64D 7/00* (2013.01); *B64D 25/02* (2013.01); *A61G 2220/10* (2013.01)

(56) References Cited

U.S. PATENT DOCUMENTS

| | | | | |
|---|---|---|---|---|
| 6,763,835 | B1 * | 7/2004 | Grove | A62B 17/04 128/857 |
| 2009/0151058 | A1 * | 6/2009 | Farnworth | A62B 31/00 2/457 |
| 2015/0067999 | A1 | 3/2015 | Stefanek et al. | |

OTHER PUBLICATIONS

ISA/US, English language International Search Report, Form PCT/ISA/210 for Int'l Application PCT/EP2018/022674, dated Aug. 13, 2018, USPTO, Alexandria, VA. (1 page).

ISA/US, English language Written Opinion of the Int'l Searching Authority, Form PCT/ISA/237 for Int'l Appln PCT/EP2018/022674, dated Aug. 13, 2018, USPTO, Alexandria, VA. (4 pages).

* cited by examiner ial rescues. The PIU of this invention is useful to safely
MARINE RESCUE PATIENT ISOLATION APPARATUS

BACKGROUND OF THE INVENTION

This invention relates generally to contaminant isolation and, more particularly, to an isolation apparatus for holding and transporting contaminated persons.

At present the Coast Guard does not have an approved capability to transport chemically or biologically contaminated patients without exposing the crew and aircraft to potential contamination. Thus there is a continuing need for an improved isolation apparatus, particularly for use in marine rescues.

SUMMARY OF THE INVENTION

A general object of the invention is to provide an improved patient isolation unit (PIU), such as for use in marine rescues. The PIU of this invention is useful to safely transport personnel exposed to, or potentially exposed to, an identified and/or known infectious agent or chemical warfare agent (CWA) on marine vessels and/or aircraft such as Coast Guard boasts, cutters and aircraft. This apparatus of this invention can be used to move a non-critical patient when operational concerns dictate and/or treatment-in-place is not available. The PIU of embodiments of this invention provides isolation of a contagious patient during air and ground transport, and can be used for hoisting operations. In particular embodiments, the PIU is compatible with wire rescue baskets conforming in shape to the human body and into which an injured, sick, or disabled person can be safely strapped, such as the Stokes litter rescue basket, and also the NATO litter and Gurney systems, for hoisting and fit in the cabin space for both the MH-60 and MH-65 rotary wing aircraft.

Embodiments of this invention provide an isolation apparatus for transporting a contaminated person, comprising: an enclosure sealed against releasing chemical, biological, and radiological agents, and including a plurality of vapor permeable and liquid tight flexible panels each formed of a selectively permeable material and sealed by gas tight and liquid tight seams, and defining a transport chamber for receiving the contaminated person, and a closable opening providing access to the transport chamber.

Embodiments of this invention include an enclosure having a first end and an opposite second end along a longitudinal centerline of the enclosure, the enclosure including one or more tapered side walls extending from the first end toward the second end, wherein the first end has a diameter less than the second end. The enclosure can have a rounded first end and a rounded second end, and the enclosure at least partially tapered from the first end toward the second end. The first end and/or the second end can be hemispherical. The first end desirably has a first diameter that is greater than a second diameter at the second end. The first end desirably includes a transparent window formed of a laminate film.

A gas tight and liquid tight fastener desirably closes the closable opening. The closable opening desirably includes a gas and liquid tight zipper extending along one side and both the first end and the second end. The zipper can include an external zipper flap and an internal zipper flap, the internal zipper flap including a hook and loop fastener to fasten to the enclosure. A transparent window adjacent the zipper bottom stop can be used to see the zipper is fully closed.

Embodiments of this invention further include an isolation apparatus for transporting a person, with a litter rescue basket enclosure sealed against releasing chemical, biological, and radiological agents, and defining a transport chamber for receiving the person. The enclosure includes a first end and a rounded second end, wherein the enclosure is at least partially tapered from the first end toward the second end, and the first end includes a bulbous top portion including a patient head window. Two support ribs are connected to external sides of the enclosure, wherein the support ribs extend curved across the head window and cross each other over the head window.

Other objects and advantages will be apparent to those skilled in the art from the following detailed description taken in conjunction with the appended claims and drawings.

DETAILED DESCRIPTION OF THE INVENTION

Figure 1:
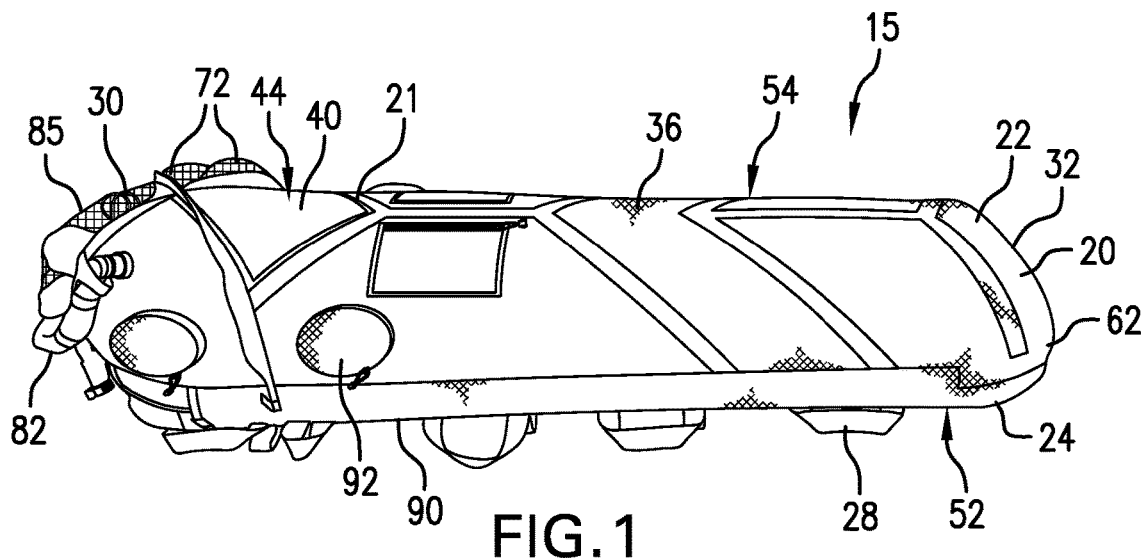
FIG. 1 is a side view of an isolation apparatus according to one embodiment of this invention.
Figure 2:
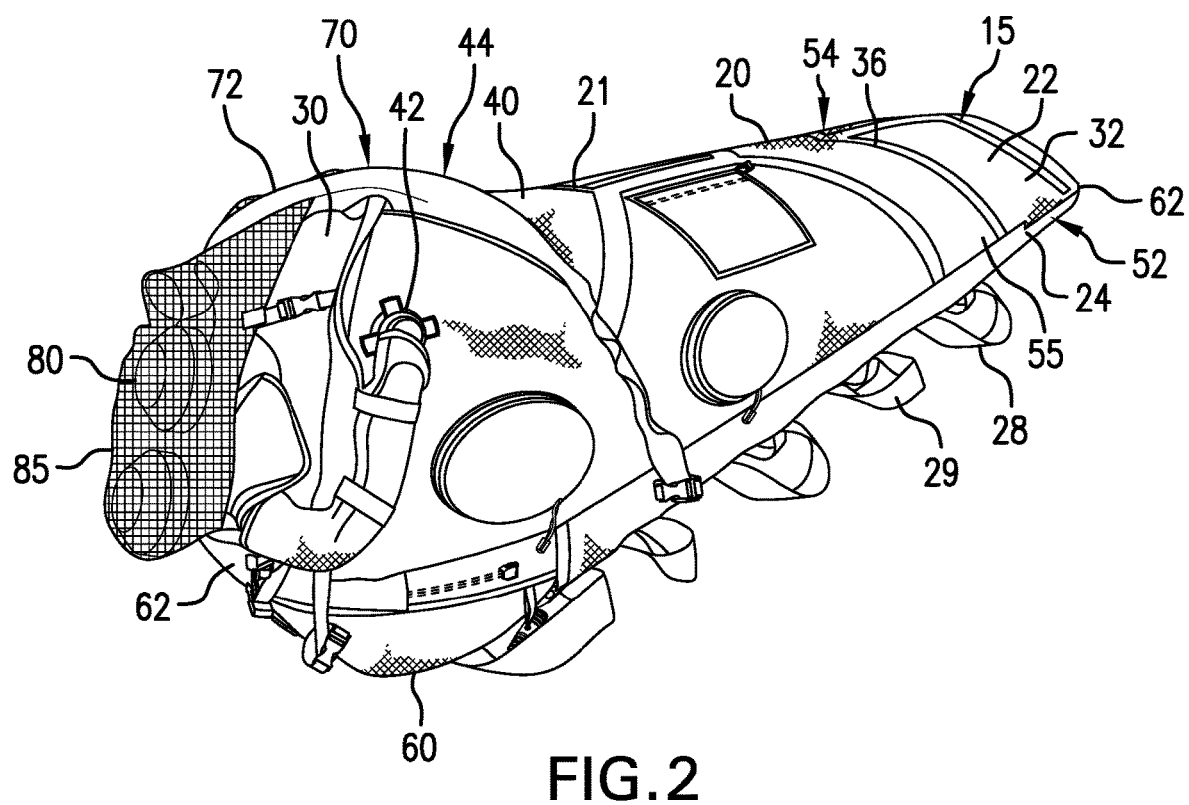
FIG. 2 is a perspective end view of the isolation apparatus according to FIG. 1.
Figure 3:
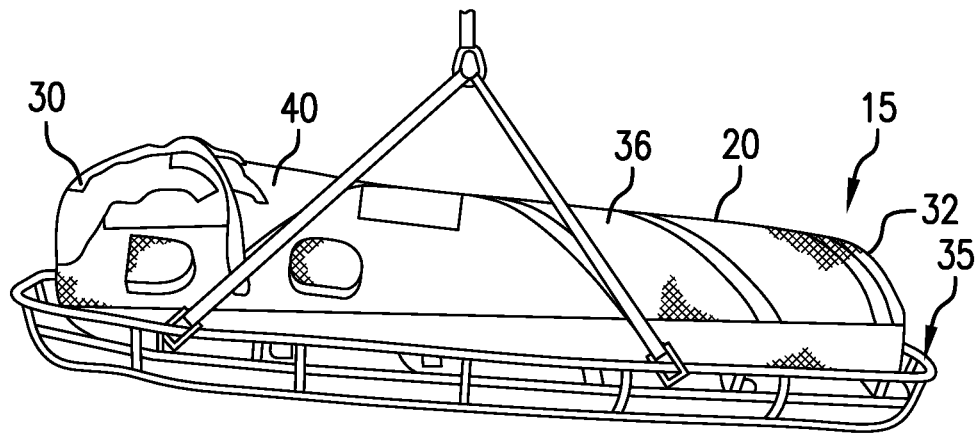
FIG. 3 shows the isolation apparatus according to FIG. 1 in a litter basket.
Figure 4:
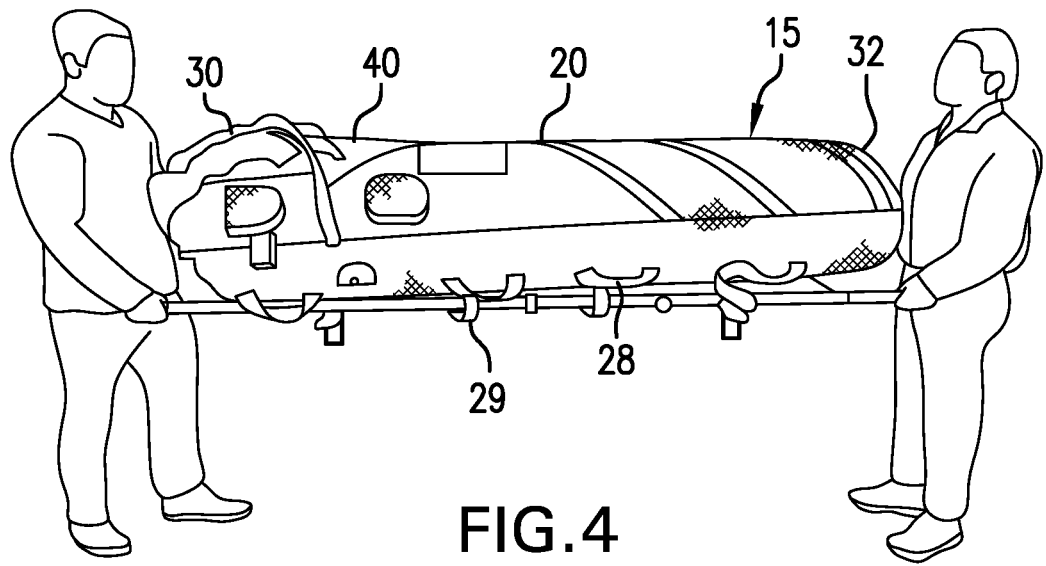
FIG. 4 shows the isolation apparatus according to FIG. 1 carried on a rescue litter/stretcher.
Figure 5:
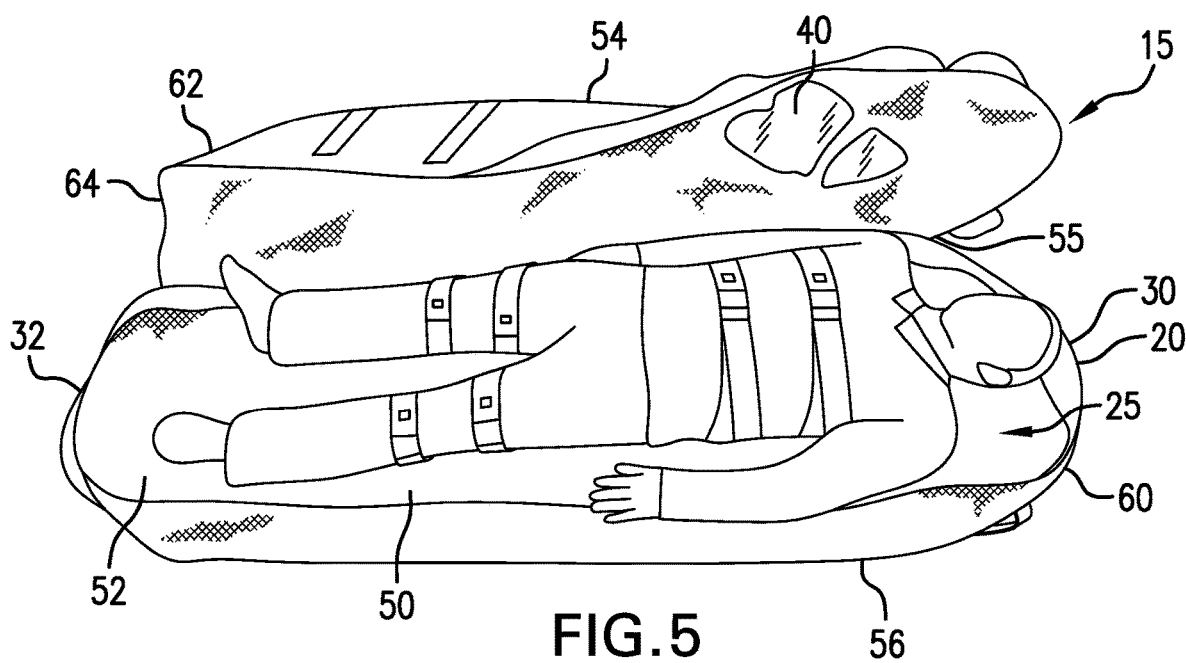
FIG. 5 shows the isolation apparatus according to FIG. 1 in an open configuration.

The present invention provides an isolation apparatus, such as shown in FIGS. 1 and 2, designed for marine rescue applications, such as shown in FIGS. 3 and 4, particularly those needing chemical warfare agent and/or biological pathogen barrier protection. The isolation apparatus 15 of FIGS. 1 and 2 includes an enclosure 20 sealed against releasing chemical, biological, and/or radiological agents. The enclosure is formed of a plurality of vapor permeable and liquid tight flexible panels, such as panels 22 and 24, each formed of a selectively permeable material and sealed by gas tight and liquid tight seams 21, and defining a transport chamber 25, as shown in FIG. 5, for receiving the person.

In embodiments of this invention, the isolation apparatus 15 has a unique tapered tubular shape with a hemispherical first end 30 and second end 32, specifically designed to fit within a standard Stokes lifting basket 35 as shown in FIG. 3. The size, shape, and/or locations of carry straps 28 of the apparatus are also compatible with standard marine rescue equipment, such as extending from the bottom section 52 and including basket-attachment loops 29, as shown in FIGS. 3 and 4. The upper section 54 of the enclosure 20 in FIGS. 1 and 2 has curved or rounded side walls curved outward between an upper longitudinal centerline and the closable opening and a bottom section 52.

Figure 9:
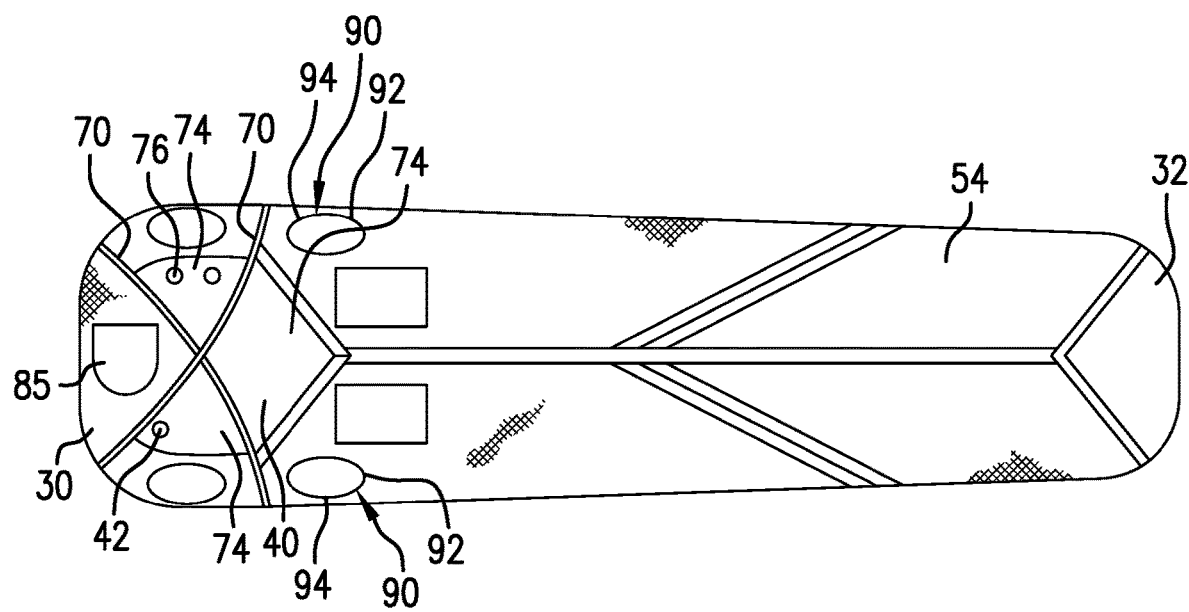
FIG. 9 is a top view of an isolation apparatus according to one embodiment of this invention.

In embodiments of this invention, the isolation apparatus is at least partially, and desirably mostly or fully formed of selectively permeable material that provides a chemical warfare agent resistance and particulate barrier with respect to biological pathogens and radiological particulates. Suitable materials are desirably breathable, so perspiration vapor can escape to reducing heat stress, and include Gore® Chempak® materials. A heat bonding process is used for seaming; providing a 100% seal, which is superior to sewn technologies. A membrane barrier envelope is desirably operated in a positive pressure mode to prevent the spread of contagious pathogens from the unit to the outside environment. The apparatus can also protect an immune-compromised patient by preventing outside pathogens from entering the system. The primary filters for removal of contamination are CBRN (chemical/biological/radiological/nuclear) filter canisters which are mounted on exhaust ports, such as shown in FIG. 9. The isolation apparatus of embodiments of this invention meets NFPA 1994-2012 STD for Class 3 (Standard on Protective Ensembles for First Responders to CBRN Terrorism Incidents). The isolation apparatus material is water repellent which offers distinctive advantages over charcoal impregnated fabrics with respect to CWA resistance, and thus is uniquely suited for marine operations.

The isolation apparatus of embodiments of this invention optionally includes protective panels 36 attached to a top section 54 as needed to provide abrasion resistance against lifting cables used in rescue operations. Rounded or curved side walls also limit contact and abrasion. Strips of reflective material 38 can be attached to the top section to provide visibility in low light and adverse weather conditions.

The isolation apparatus 15 of FIGS. 1 and 2 desirably includes a patient head window 40 formed of a multi-layer plastic laminate film 42. As shown in FIGS. 1 and 2, the first end 30 includes a bulbous top portion 44 that includes the rounded or curved window 40. The window film desirably offers superior CWA resistance and can allow an air inlet/outlet port 42 that can be fully sealed without compromising the Gore® Chempak®.

The apparatus enclosure 20 includes a pressure sealed closable opening 50 that provides access to the transport chamber 25. As shown in FIGS. 1 and 2, the opening 50 separates a bottom section 52 and a top section 54 of the enclosure 20. The closable opening 50 and the fastener used to close the opening 50 desirably extend fully along a first side 56 of the enclosures and around each of the first and second ends 30 and 32. The connection of the top and bottom sections on an opposing second side 58 forms a hinge 55 allowing for a suitcase or clamshell opening as shown in FIG. 5.

Figure 6:
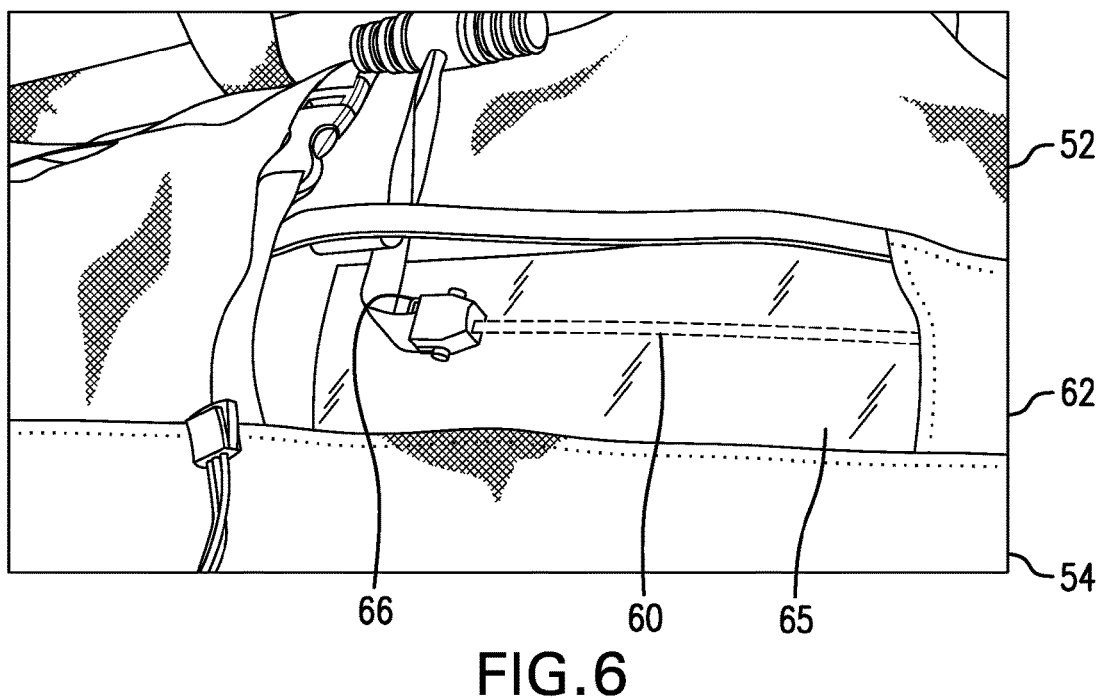
FIG. 6 shows a zipper of the isolation apparatus according to FIG. 1.

The opening 50 can be closed and sealed by any suitable resealable fastener, such as a zipper closure, and preferably a gas and liquid tight zipper 60. The zipper runs along the first side 56 and around both ends 30 and 32 to form a door flap of the top section 54, to provide the suitcase style opening shown in FIG. 5. An external zipper flap 62 can be attached to, for example, the top section 54 and extend down over the zipper 50 to provide mechanical protection. The zipper flap 62 can incorporate a clear window 65 at and over the zipper closed end stop 66 to allow visual verification of full zipper closure. An internal zipper flap 64 of the Gore® Chempak® material can be used to provide extra CWA leakage protection, and can be held in place with a suitable hook & loop fastener along the inside of the enclosure 20. FIG. 6 shows an exemplary zipper 60 and the clear window 65 as the end portion of the zipper flap 62.

In embodiments of this invention, as shown in FIGS. 1 and 2, the isolation apparatus 15 includes support ribs 70 to help keep the desired enclosure shape of the apparatus. The ribs 70 curve around the curved top section 54 and cross each other at an angle, such as at an angle of about 45°-90°. As shown in FIGS. 1 and 2, the ribs 70 are generally perpendicular and extend at least partially over the head window 40.

Two or more support rib pockets 72 are attached to the top section 54 at the head end 30. The pockets 72 traverse the top section 54 from side to side on a diagonal to the longitudinal axis and are mutually perpendicular like the ribs 70. The pockets are attached across the apparatus 15, and have an internal passageway, open at one end, for receiving the ribs 70. The ribs 70 are flexible to fit in the pockets and are also removable. In embodiments of this invention, the open ends of the rib pockets 72 desirably include a pocket, fold over, and/or are secured with a small snap buckle strap or equivalent, to secure in place therein the corresponding one of the ribs 70. A crossed rib pocket design desirably allows the unit to be folded flat without removing the ribs, but still provides support to keep the top section 54 suspended above the patients head at all times.

In FIGS. 1, 2, and 9, the head window 40 is divided into more than one window panel 74 by the rib pockets 72. The rib pockets 72 can be attached to the window 40 itself, or at sealed seams between the individual panels 74.

Figure 7:
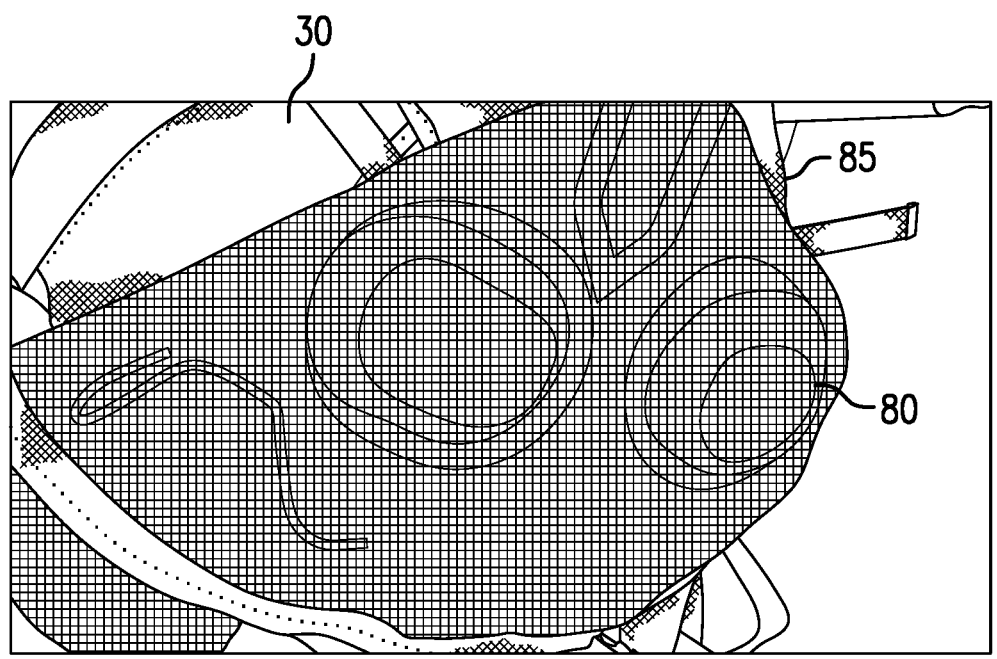
FIG. 7 shows a respirator on the isolation apparatus according to FIG. 1.

Airflow to the patient can be provided by respirator 80, for example, a battery-powered PAPR (powered air-purifying respirator) blower fitted with HE/P-100 filters, such as shown at a head end 30 of the apparatus 15 in FIGS. 1 and 2. A 4 cfm (min) rated blower provides approximately 20 to 38 air changes per hour within the isolator depending on patient volume. The apparatus 15 can be operated with positive or negative pressure. A pocket 85 made of protective mesh, as shown in FIG. 7, or other material is included to hold and/or protect critical externally mounted components such as a blower, filter, hose 82, and/or battery pack against abrasion from lifting cables and/or prop wash. In some embodiments, a blower mounting is specifically tailored to fit into a Stokes litter basket, and can also incorporate specific straps for securing to the litter.

In FIGS. 1, 2, and 9, the respirator 80 and pocket 85 are disposed at the first end 30 and between ends of the two ribs 70. The respirator hose 82 extends to an inlet port 42 connected to and through one of the side window panels 74 between the ribs 70. A filtered outlet port 76, such as including a filter discussed above, can be connected to and through an opposing side window panel 74 between the ribs 70. Various and alternative sizes, shapes, amounts, and configurations of the ribs, head window, respirator, and inlet/outlet ports are available depending on need.

Figure 8:
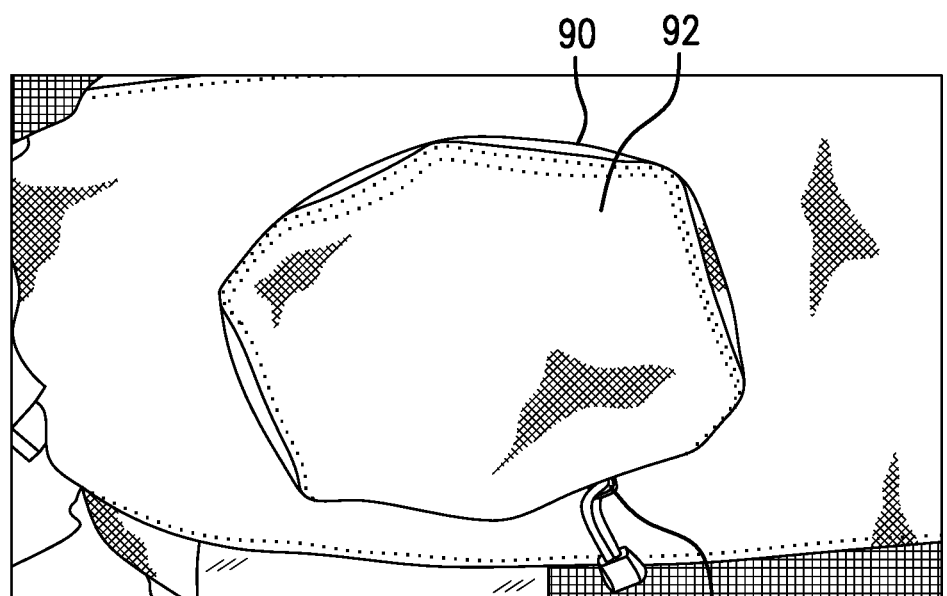
FIG. 8 shows a glove port of the isolation apparatus according to FIG. 1.

In some embodiments of this invention, the isolation apparatus 15 includes glove ports 90 for gloved access to the transport chamber. The glove ports 90 can be openings or have built in gloves, such as fabricated from the Gore® Chempak® material. Glove port caps 92 are attached over the glove ports and sealed/openable via water repellent zippers 94, as shown in FIG. 8, and provide protection against accidental removal from prop wash, lifting cables, etc.

Thus, the invention provides an isolation apparatus for holding and transporting contaminated persons that is particularly suited for marine use and is usable with marine rescue baskets.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

The invention claimed is:

1. An isolation apparatus for transporting a person, comprising:
   an enclosure sealed against releasing chemical, biological, and radiological agents, and including a plurality of vapor permeable and liquid tight flexible panels each formed of a selectively permeable material and sealed by gas tight and liquid tight seams, and defining a transport chamber for receiving the person;
   the enclosure including a closable opening providing access to the transport chamber; and
   the enclosure including a rounded first end and a rounded second end, and the enclosure at least partially tapered from the first end toward the second end.

2. The apparatus of claim 1, wherein the first end has a first diameter that is greater than a second diameter at the second end.

3. The apparatus of claim 1, wherein the isolation apparatus comprises dimension configured to fit within a Stokes basket.

4. The apparatus of claim 1, wherein the first end comprises a bulbous top portion including a patient head window.

5. The apparatus of claim 1, wherein the closable opening comprises a gas tight and liquid tight fastener that extends around each of the first and second ends.

6. The apparatus of claim 1, wherein the closable opening comprises a gas and liquid tight zipper extending along one side and around both the first end and the second end.

7. The apparatus of claim 6, wherein the zipper includes an external zipper flap and an internal zipper flap, the internal zipper flap including a hook and loop fastener.

8. The apparatus of claim 6, further comprising an external zipper flap including a transparent zipper window adjacent a zipper stop.

9. The apparatus of claim 1, further comprising glove port openings in the enclosure, wherein each of the glove port openings is covered by a zippered glove port cap.

10. The apparatus of claim 1, wherein the first end comprises a transparent head window formed of a laminate film.

11. The apparatus of claim 10, further comprising two support ribs extending across each other over the head window.

12. The apparatus of claim 11, further comprising rib pockets connected to the enclosure to removably receive the support ribs.

13. The apparatus of claim 12, wherein each of the rib pockets includes an open end with a fastenable closure.

14. The apparatus of claim 11, further comprising a pocket on an outer surface of the enclosure at the first end and between ends of the support ribs.

15. The apparatus of claim 14, further comprising a respirator disposed in the pocket.

16. The apparatus of claim 15, further comprising a respirator inlet in the head window configured to receive a respirator hose.

17. An isolation apparatus for transporting a person, comprising:
   a litter basket enclosure sealed against releasing chemical, biological, and radiological agents, and including a plurality of vapor permeable and liquid tight flexible panels each formed of a selectively permeable material and sealed by gas tight and liquid tight seams, and defining a transport chamber for receiving the person;
   the enclosure including a closable opening providing access to the transport chamber;
   the enclosure including a first end and a rounded second end, wherein the enclosure is at least partially tapered from the first end toward the second end, wherein the first end comprises a bulbous top portion including a patient head window; and
   the enclosure including two support ribs each connected to external sides of the enclosure, wherein the support ribs extend curved across the head window and cross each other over the head window.

18. The apparatus of claim 17, further comprising:
   a pocket on an outer surface of the enclosure at the first end and between ends of the support ribs; and
   a respirator disposed in the pocket and connected to the transport chamber.

19. The apparatus of claim 17, wherein the closable opening comprises a zipper, an external zipper flap over the zipper, and an internal zipper flap over the zipper within the transport chamber, the external zipper flap including a transparent zipper window adjacent a zipper stop and the internal zipper flap including a hook and loop fastener to fasten the flap over the zipper.

20. The apparatus of claim 17, further comprising glove port openings in the enclosure, wherein each of the glove port openings is covered by a zippered glove port cap.

* * * * *